United States Patent
Mooshofer

(10) Patent No.: US 10,222,352 B2
(45) Date of Patent: Mar. 5, 2019

(54) METHOD AND DEVICE FOR IMPROVING THE SAFT ANALYSIS WHEN MEASURING IRREGULARITIES

(71) Applicant: SIEMENS AKTIENGESELLSCHAFT, Munich (DE)

(72) Inventor: Hubert Mooshofer, Munich (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 577 days.

(21) Appl. No.: 14/761,833

(22) PCT Filed: Oct. 23, 2013

(86) PCT No.: PCT/EP2013/072181
§ 371 (c)(1),
(2) Date: Jul. 17, 2015

(87) PCT Pub. No.: WO2014/121858
PCT Pub. Date: Aug. 14, 2014

(65) Prior Publication Data
US 2015/0346157 A1    Dec. 3, 2015

(30) Foreign Application Priority Data
Feb. 7, 2013    (DE) .................. 10 2013 201 975

(51) Int. Cl.
*G01N 29/04*    (2006.01)
*G01N 29/24*    (2006.01)
(Continued)

(52) U.S. Cl.
CPC .......... *G01N 29/04* (2013.01); *G01N 29/069* (2013.01); *G01N 29/0645* (2013.01);
(Continued)

(58) Field of Classification Search
None
See application file for complete search history.

(56) References Cited

U.S. PATENT DOCUMENTS 3,939,697 A * 2/1976 Lund ................. A61B 8/08
73/614
5,278,757 A    1/1994 Hoctor et al.
(Continued)

FOREIGN PATENT DOCUMENTS

CN    1954235 A    4/2007    ............ G01S 15/89
CN    102043016 A    5/2011    ............ G01N 29/06
(Continued)

OTHER PUBLICATIONS

Chinese Office Action, Application No. 201380072507.1, 12 pages, dated Dec. 7, 2016.
(Continued)

*Primary Examiner* — Michael Lebentritt
(74) *Attorney, Agent, or Firm* — Slayden Grubert Beard PLLC

(57) ABSTRACT

The invention relates to a method and to a corresponding device in which irregularities regarding each detected measurement position within a measurement surface are detected using a local measurement density. Each echo signal received in response to each detected measurement position is then weighted in order to generate an image using a data processing device such that the irregularities are adjusted.

22 Claims, 2 Drawing Sheets

(51) Int. Cl.
| | |
|---|---|
| *G01N 29/34* | (2006.01) |
| *G01N 29/44* | (2006.01) |
| *G01S 15/89* | (2006.01) |
| *G01N 29/06* | (2006.01) |
| *G01N 29/26* | (2006.01) |
| *G01N 29/265* | (2006.01) |
| *G01S 7/52* | (2006.01) |

(52) U.S. Cl.
CPC ......... *G01N 29/0672* (2013.01); *G01N 29/24* (2013.01); *G01N 29/262* (2013.01); *G01N 29/265* (2013.01); *G01N 29/343* (2013.01); *G01N 29/449* (2013.01); *G01N 29/4463* (2013.01); *G01S 7/5205* (2013.01); *G01S 15/8936* (2013.01); *G01S 15/8997* (2013.01)

(56) References Cited

U.S. PATENT DOCUMENTS

| | | | | |
|---|---|---|---|---|
| 5,699,803 | A * | 12/1997 | Carodiskey | A61B 8/4281 |
| | | | | 128/898 |
| 5,952,577 | A * | 9/1999 | Passi | G01N 29/069 |
| | | | | 600/445 |
| 7,509,861 | B2 | 3/2009 | Masotti et al. | 73/659 |
| 8,248,595 | B2 | 8/2012 | Ochiai et al. | 356/237.2 |
| 9,402,601 | B1 * | 8/2016 | Berger | A61B 8/4472 |
| 9,404,904 | B2 * | 8/2016 | Puckett | G01N 27/90 |
| 2004/0015079 | A1 * | 1/2004 | Berger | A61B 8/546 |
| | | | | 600/437 |
| 2004/0225220 | A1 * | 11/2004 | Rich | A61B 8/00 |
| | | | | 600/446 |
| 2007/0150238 | A1 * | 6/2007 | Struempler | G01N 27/90 |
| | | | | 702/189 |
| 2008/0121040 | A1 | 5/2008 | MacLauchlan et al. | |
| 2009/0314089 | A1 * | 12/2009 | Brignac | G01N 29/226 |
| | | | | 73/622 |
| 2011/0113885 | A1 | 5/2011 | Ueda et al. | |
| 2012/0024067 | A1 * | 2/2012 | Oberdoerfer | G01N 29/069 |
| | | | | 73/632 |
| 2012/0036934 | A1 * | 2/2012 | Kroning | G01N 29/043 |
| | | | | 73/628 |
| 2012/0192650 | A1 | 8/2012 | Tsai et al. | 73/602 |
| 2012/0296215 | A1 | 11/2012 | Brown et al. | |
| 2013/0080086 | A1 * | 3/2013 | Oberdoerfer | G01N 29/262 |
| | | | | 702/56 |
| 2013/0276540 | A1 * | 10/2013 | Fujiwara | G01N 29/043 |
| | | | | 73/629 |
| 2013/0297232 | A1 | 11/2013 | Euler et al. | 702/40 |
| 2014/0165730 | A1 * | 6/2014 | Na | G01N 29/0645 |
| | | | | 73/588 |
| 2014/0204702 | A1 * | 7/2014 | Ratering | G01N 29/0609 |
| | | | | 367/8 |
| 2014/0276060 | A1 * | 9/2014 | Hayashi | A61B 8/14 |
| | | | | 600/443 |
| 2015/0153310 | A1 * | 6/2015 | Yamamoto | G01N 29/0645 |
| | | | | 73/627 |
| 2015/0292916 | A1 * | 10/2015 | Viren | G01D 5/347 |
| | | | | 250/231.1 |
| 2015/0362593 | A1 * | 12/2015 | Goldammer | G01N 29/069 |
| | | | | 367/7 |
| 2016/0139082 | A1 * | 5/2016 | Ross | B29C 66/9672 |
| | | | | 73/588 |
| 2016/0363436 | A1 * | 12/2016 | Clark | G01B 11/002 |

FOREIGN PATENT DOCUMENTS

| | | | | |
|---|---|---|---|---|
| CN | 102613989 A | | 8/2012 | A61B 8/00 |
| DE | 102009050160 A1 | | 5/2011 | |
| DE | 102013200974 A1 | | 7/2014 | |
| EP | 0105966 A1 | | 4/1984 | |
| JP | 51128183 A | | 11/1976 | A61B 10/00 |
| JP | 5975147 A | | 4/1984 | G01N 29/06 |
| JP | 61134663 A | | 6/1986 | G01N 29/04 |
| KR | 20110103376 A | | 9/2011 | G01N 29/04 |
| WO | 2012/100999 A1 | | 8/2012 | G01N 21/84 |

OTHER PUBLICATIONS

Korean Office Action, Application No. 2016091951075, 4 pages, dated Dec. 20, 2016.
Korean Office Action, Application No. 1020157023093, 4 pages, dated Jun. 16, 2016.
International Search Report dated Feb. 3, 2014 in related International Application No. PCT/EP2013/072181.
German Search Report dated Nov. 4, 2013 in related German Application No. 102013201975.0.

* cited by examiner

METHOD AND DEVICE FOR IMPROVING THE SAFT ANALYSIS WHEN MEASURING IRREGULARITIES

CROSS REFERENCE TO RELATED APPLICATIONS

This application is based on and hereby claims priority to International Application No. PCT/EP2013/072181 filed on Oct. 23, 2013 and German Application No. 10 2013 201 975.0 filed on Feb. 7, 2013, both applications are incorporated by reference herein in their entirety.

BACKGROUND

Described below are a method and a device for ultrasonic testing of a test object.

Very varied ultrasonic testing methods are known for nondestructive testing of test objects. The analysis technique SAFT (Synthetic Aperture Focusing Technique) is known for better localization and separation of defects in nondestructive testing with ultrasound. Inspection is performed in this case as in known ultrasonic testing, but the data are recorded without rectification. In the subsequent analysis of the measurement data, amplitude sums are determined from a multiplicity of measurement signals for respective small volume elements, which are also denoted as so-called voxels. Ultrasonic testing can be used with the aid of SAFT analysis, for example given manual movement of a probe which emits the ultrasonic pulses and receives the corresponding echo signals. Such SAFT testing is described, for example, in DE 10 2013 200974.7.

It is possible through the use of so-called phased array probes for test objects to be scanned not just mechanically but also electronically, that is to say a plurality of measurements are carried out in a defined grid by a kind of electronic displacement of the active zone of the probe. In the case of a stationary probe, data which have been recorded with the same electronic scan can be evaluated with the SAFT analysis. This works both for an unmoved probe and in the case of a probe moved during the electronic scan when the exact transmitted and received position as well as the angle of incidence and focusing at the reconstruction instant are known.

SUMMARY

In one aspect improved, in particular freehand-guided, ultrasonic testing of a test object is enabled with the aid of SAFT analysis. In particular, artifacts or measuring errors produced in manual free guidance of a probe are intended to be effectively reduced or removed in the SAFT evaluation.

The method according to the invention for ultrasonic testing of a test object described below includes moving a test object along a test object surface and emitting ultrasonic pulses into the test object by the probe; receiving respective echo signals corresponding to the emitted ultrasonic pulses by the probe; producing an image of a prescribed test area of the test object on the basis of superposing and averaging amplitude values of the received echo signals by a data processing device. In other words, the method for ultrasonic testing of a test object includes the operations required in a SAFT analysis, the respective positions of the probe for the emission of the ultrasonic signals and/or for the reception of the corresponding echo signals additionally being detected by a detecting device, and the respectively detected positions of the probe when producing the image of the test area of the test object additionally being taken into account.

In accordance with a first aspect, a freely guided probe is moved manually along a test object surface and measurements are executed within a measurement surface including subareas by emitting ultrasonic pulses into the test object by the probe, and receiving respective echo signals corresponding to the emitted ultrasonic pulses by the probe; an image is produced of a prescribed test area of the test object on the basis of superposing and averaging amplitude values of the received echo signals by a data processing device; a respective measurement position of the probe is detected by a detecting device; the respectively detected measurement positions of the probe are taken into account when producing the image of the test area of the test object; an evaluation variable is determined for detecting irregularities with regard to the respectively detected measurement positions within the measurement surface by the data processing device; with the aid of the evaluation variable each echo signal received in relation to the respectively detected measurement position is weighted for the production of the image by the data processing device in such a way that the irregularities are compensated.

In accordance with a second aspect, there is proposed a device for ultrasonic testing of a test object, including a probe which can be moved manually freely along a test object surface and within a measurement surface including subareas, and measures by emitting ultrasonic pulses into the test object and receiving respective echo signals corresponding to the emitted ultrasonic pulses; a detecting device which detects a respective measurement position of the probe; and a data processing device which produces an image of a prescribed test area of the test object on the basis of superposing and averaging amplitude values of the received echo signals, and which takes account of the respectively detected measurement positions of the probe when producing the image of the test area of the test object; wherein, by at least one evaluation variable for detecting irregularities with regard to the respectively detected measurement positions within the measurement surface the data processing device weights each echo signal received in relation to the respectively detected measurement position for the production of the image in such a way that the irregularities are compensated.

It has been realized that in manual guidance a probe is not guided precisely and measurements are executed in a fluctuating grid and/or along crooked paths such that artifacts are produced in this way. In order to reduce artifacts, an echo signal at each measurement point should not be used directly for SAFT evaluation. The aim is that echo signals are selected and/or weighted in accordance with a density and distribution of measurement points on a measurement surface so that all parts of the measurement surface contribute as evenly as possible to each reconstructed voxel and/or test area of the test object. It is a precondition in this case that reliable position information is available for each individual measurement.

The solution provides an improved SAFT evaluation of tests with the aid of a probe guided in freehand fashion. Likewise, artifacts can be effectively reduced and a signal-to-noise ratio SNR of the SAFT result can be effectively increased. It is likewise possible to compensate for irregularities, the causes of which do not lie in the freehand guidance of the probe but, for example, are caused by coupling fluctuations.

In accordance with one embodiment, it is possible to determine a local measurement density as an evaluation variable and to perform weighting in such a way that echo signals of measurement positions with relatively large local measurement density are given relatively small weightings.

In accordance with a further embodiment, it is possible to perform a determination of the local measurement density from a respective number of detected measurement positions per unit area of the measurement surface, or per unit length of at least one scan line of the measurement surface.

In accordance with a further embodiment, it is possible to perform weighting in such a way that echo signals of measurement positions are weighted in an inversely proportional fashion to the local measurement density.

In accordance with a further embodiment, it is possible to determine the local measurement density by summing all of the reciprocals of all of the distances of a detected measurement position in relation to all other detected measurement positions within a prescribed first radius.

In accordance with a further embodiment, it is possible to weight in such a way that echo signals of measurement positions with relatively large local measurement density are weighted with zero.

In accordance with a further embodiment, it is possible to perform redetermination of the local measurement density within a prescribed second radius around the measurement positions whose echo signals have been weighted with zero.

In accordance with a further embodiment, it is possible to perform repeated omission of measurement positions weighted with zero and redetermination of the local measurement density as long as a prescribed minimum measurement density is not undershot.

In accordance with a further embodiment, it is possible to perform determination of a homogeneous contribution of all subareas of the measurement surface as evaluation variable and weighting in such a way that the echo signals of measurement positions contribute as equally as possible to the image.

In accordance with a further embodiment, it is possible to perform detection of the respective measurement position of the probe upon emission of the ultrasonic signal and/or upon reception of the corresponding echo signal.

BRIEF DESCRIPTION OF THE DRAWINGS

These and other aspects and advantages will become more apparent and more readily appreciated with the aid of two exemplary embodiments described below with reference to the accompanying drawings of which.

DETAILED DESCRIPTION OF THE PREFERRED EMBODIMENT

Figure 1:
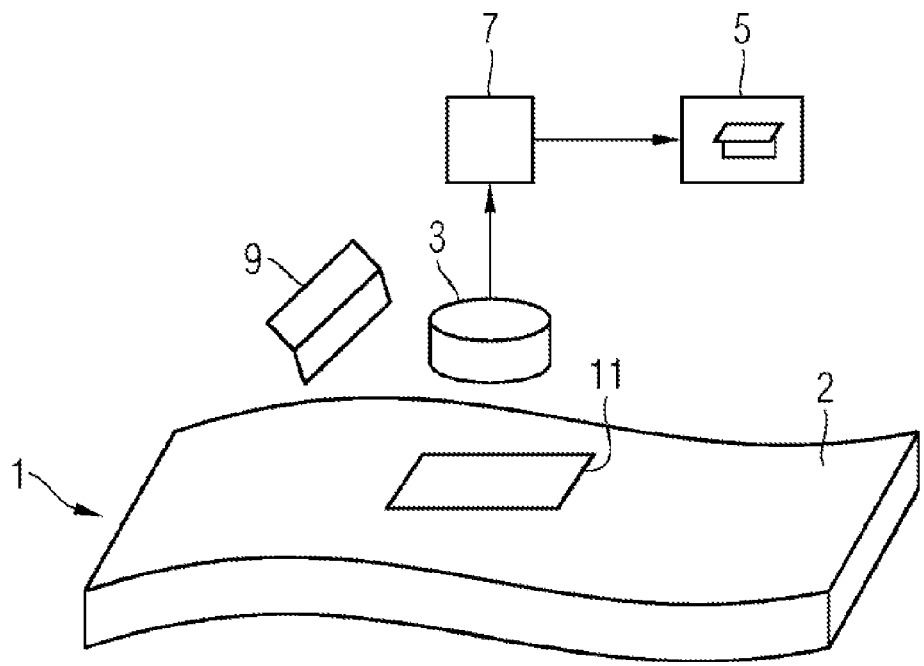
FIG. 1 shows an exemplary embodiment of the device.

Reference will now be made in detail to the preferred embodiments of the present invention, examples of which are illustrated in the accompanying drawings, wherein like reference numerals refer to like elements throughout.

FIG. 1 shows a first exemplary embodiment of a device, the position of a probe 3 on a surface 2 of a test object 1 being measured throughout the duration of the test. The measurement of the respective position is performed in this case within comparatively short intervals and with a defined temporal reference relative to the ultrasonic pulses emitted for inspection of the test object 1. The position measurement is may be performed by a detecting device 9 in each case whenever an ultrasonic pulse is emitted. In addition, it is also possible in each case for a position measurement to be performed when the echo signal corresponding to the emitted ultrasonic pulse is received.

As a function of the detected or measured respective positions of the probe 3, a respectively instantaneous position of the probe 3 is determined, such as at the time of a respective emission of the ultrasonic pulse, and is used in the SAFT analysis in order to determine a distance between a voxel to be reconstructed and the actual measurement position.

The device and the method for ultrasonic testing of a test object are intended to be applied with the aid of SAFT analysis for a probe 3 which is moved, in particular guided in freehand fashion. The probe 3 can be moved manually in this case along the test object surface 2. In particular, in the method the probe 3 can be guided freely on the test object surface 2. The localization of defects within the test object 1 is substantially improved by the method, individual defects being better distinguished from one another, and the signal-to-noise ratio being improved, particularly in the case of manual testing, in particular in the case of testing by freehand guidance. The result of this in the case of the production of the image 5 of the test area of the test object 1 is an improved resolution of group displays, that is to say of individual displays lying near one another which could not be separated from one another without SAFT analysis, and therefore would be assessed as a larger display, and, in particular, an improved detection of small defects. Here, small defects are to be understood as defects having a dimension which is small in comparison to the wavelength used for the ultrasonic pulses. In addition, the test results 5 which are achieved with the method can be interpreted in a particularly intuitive fashion by referencing a three-dimensional digital model of the test object.

The measured positions and orientations, and the respective temporal reference can be used to calculate the instantaneous position and orientation of the probe 3 at the instant of each ultrasonic pulse, and can be used in the so-called SAFT analysis in order to determine the distance between the reconstructed respective voxel and the measurement position. In this case, the detected position and orientation of the probe 3 can be used to determine the center position of the active aperture of the probe when ultrasonic signals are being emitted, and to take account of the center position during the production of the image of the test area of the test object 1. Here, the active aperture is to be understood as the portion of the probe 3 which serves as effective transmitting surface or receiving surface. A spatial offset between the respective position measurement and the position of the probe 3 can be extrapolated by calculation with the aid of the detected information relating to the probe orientation.

In an embodiment of the device, it can be provided that the detecting device 9 includes an optical movement sensor which is attached to the probe 3 and by which the respective position relative to a reference point can be detected. By way of example, the reference point can be the position at which the probe 3 was arranged at the beginning of the ultrasonic testing. The detecting device 9 in this case may include a further optical movement sensor (not illustrated) which is attached to the probe 3 at a prescribed distance away from the other optical movement sensor, and by which the respective position relative to the reference point can be detected.

In a further embodiment of the device, it can be provided that the detecting device 9 includes an imaging device by which a plurality of optical marks applied to the probe 3 can be detected and, on the basis thereof, the position and orientation of the probe 3 can be determined.

A device for ultrasonic testing of a test object 1 is shown in a schematic perspective view. The device includes a probe 3 which is movable along a test object surface 2 in freehand fashion and by which it is possible to emit ultrasonic pulses into the test object 1 and to receive respective echo signals corresponding to the emitted ultrasonic pulses. Furthermore, the device includes a data processing device 7 by which it is possible to produce an image 5 of a test area of the test object 1 on the basis of superposing and averaging amplitude values of the received echo signals. In other words, the device for ultrasonic testing of the test object 1 is designed for the purpose of carrying out a so-called SAFT analysis (Synthetic Aperture Focusing Technique) within the context of ultrasonic testing of the test object 1.

FIG. 1 shows the data processing device 7 which produces an image 5 of a prescribed test area of the test object 1 on the basis of superposing and averaging amplitude values of the received echo signals; and the respectively detected measurement positions of the probe 3 are taken into account when producing the image 5 of the test area of the test object 1. The data processing device 7 weights by at least one evaluation variable for detecting irregularities with regard to the respectively detected measurement positions within the measurement surface of each echo signal, received in relation to the respectively detected measurement position, for the production of the image 5 in such a way that the irregularities are compensated. The probe 3 measures the test object 1 within a defined measurement surface 11. By way of example, the measurement surface 11 can be a planar rectangular surface.

Figure 2:
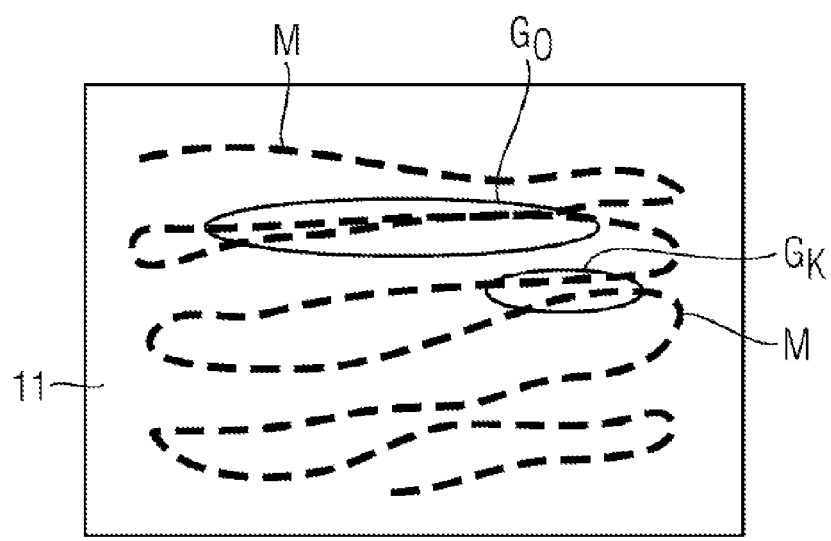
FIG. 2 shows an exemplary probe movement over a measurement surface in the context of carrying out the test.

FIG. 2 shows an exemplary embodiment of a measurement surface 11 on which measurement positions M are represented. Measurement points or measurement line segments are represented here along a meandering scan line. A movement of the probe guided in freehand fashion may be seen along the line. Overlaps of the measurement and of measurement positions M result at the framed subareas or surfaces. In this way, distributions of measurement positions M may be seen and density values can be estimated. Accordingly, a local measurement density, which can likewise be denoted as local shot density, is illustrated. In order to compensate irregularities caused by excessively high shot densities, it is now proposed to take less account of echo signals of measurement positions M with a large local measurement density line than of echo signals of measurement positions M with average or low measurement density. This can have the effect that, for example, echo signals from the area or subarea G0 are weighted with the number zero and are therefore removed completely for the purpose of producing an image. Since the relative local measurement density is certainly high in the subarea Gk, but lower than in the subarea G0, it is, for example, advantageous to attenuate echo signals there for the image and weight them as less than 100%. The exact selection of the weighting factors can be performed experimentally or determined mathematically.

Figure 3:
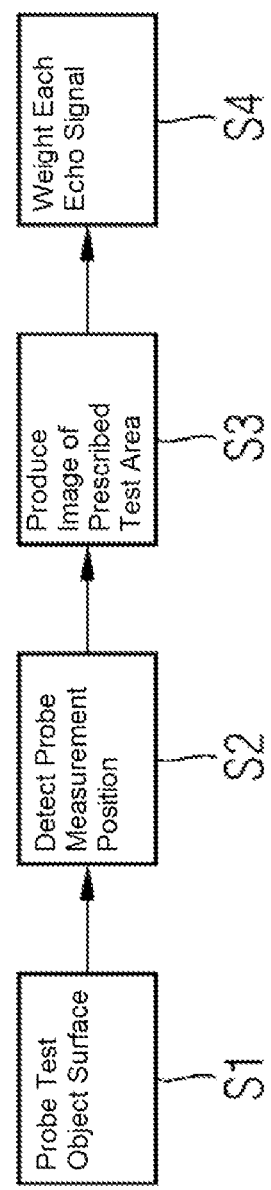
FIG. 3 shows an exemplary embodiment of the method.

FIG. 3 shows an exemplary embodiment of a method. It is possible, by way of example, to execute the following operations for ultrasonic testing of a test object. With an operation S1, a movement is performed—in particular in freehand fashion—of a probe along a test object surface, and simultaneous measurement executed within a measurement surface including subareas is performed by emitting ultrasonic pulses into the test object by the probe, and echo signals respectively corresponding to the emitted ultrasonic pulses are received by the probe. With an operation S3, an image of a prescribed test area of the test object is produced on the basis of superposing and averaging amplitude values of the received echo signals by a data processing device, with account being taken of the respectively detected measurement positions of the probe during production of the image of the test area of the test object, the detection of a respective measurement position of the probe being executed by a detecting device in an operation S2. With the aid of an evaluation variable for detecting irregularities with regard to the respectively detected measurement positions within the measurement surface, in a fourth operation S4 a weighting is executed of each echo signal, received in relation to the respectively detected measurement position, for the production of the image by the data processing device in such a way that the irregularities are compensated.

By the device and the method described for ultrasonic inspection of a test object 1, the SAFT method, which is known per se, can also be reliably applied in the case of manual guidance of a probe by carrying out in the way described detection of the position and orientation of the probe 3 during the ultrasonic testing of the test object 1, and taking it into account when producing an image 5 of an area of the test object 1 which is to be inspected.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

The invention claimed is:

1. A method for ultrasonic testing of a test object, comprising:
    moving a probe along a test object surface within a measurement surface that has subareas;
    emitting ultrasonic pulses into the test object from the probe; and
    receiving respective echo signals corresponding to the ultrasonic pulses emitted by the probe;
    producing an image of a prescribed test area of the test object based on superposing and averaging amplitude values of the respective echo signals by a data processing device;
    detecting a respective measurement position of the probe for each ultrasonic pulse emitted using a detecting device;
    taking account of the respective measurement positions of the probe when producing the image of the prescribed test area of the test object;
    determining an evaluation variable for detecting irregularities with regard to the respective measurement positions within the measurement surface by the data processing device; and
    weighting with the aid of the evaluation variable each echo signal received in relation to the respective measurement positions for the production of the image by the data processing device to compensate for the detected irregularities.

2. The method as claimed in claim 1, further comprising determining a local measurement density as the evaluation variable, and weighting the echo signals of the respective measurement positions that have relatively large local measurement densities with relatively small weightings.

3. The method as claimed in claim 2, further comprising determining the local measurement density from a representative number of the respective measurement positions per unit area of the measurement surface, or per unit length of at least one scan line of the measurement surface.

4. The method as claimed in claim 2, further comprising determining the local measurement density by summing all of the reciprocals of all of the distances of a detected measurement position in relation to all other detected measurement positions within a prescribed first radius.

5. The method as claimed in claim 2, further comprising weighting the echo signals of the respective measurement positions in inverse proportion to the local measurement density.

6. The method as claimed in claim 2, further comprising weighting the echo signals of the respective measurement positions that have relatively large local measurement densities with zero.

7. The method as claimed in claim 6, further comprising redetermining the local measurement density within a prescribed second radius around the respective measurement positions having corresponding echo signals that have been weighted with zero.

8. The method as claimed in claim 6, further comprising repeatedly omitting the respective measurement positions having echo signals that have been weighted with zero, and redetermining the local measurement density as long as a prescribed minimum measurement density is at least equal to a predetermined measurement density.

9. The method as claimed in claim 2, further comprising determining a homogeneous contribution of all of the subareas of the measurement surface as the evaluation variable and weighting the echo signals of the respective measurement positions to contribute as equally as possible to the image.

10. The method as claimed in claim 2, further comprising detecting the respective measurement positions of the probe upon at least one of emission of the ultrasonic signal and reception of the corresponding echo signal.

11. The method as claimed in claim 2, further comprising moving the probe by hand along the surface of the test object.

12. A device for ultrasonic testing of a test object, comprising:
a probe, movable along a surface of the test object and within a measurement surface having subareas, emitting ultrasonic pulses into the test object, and receiving respective echo signals corresponding to the ultrasonic pulses emitted;
a detection device detecting respective measurement positions of the probe; and
a data processing device producing an image of a prescribed test area of the test object based on superposing and averaging amplitude values of the echo signals, taking account of the respective measurement positions of the probe when producing the image of the test area of the test object, and weighting each echo signal received in relation to the respective measurement positions by at least one evaluation variable for detecting irregularities with regard to the respective measurement positions within the measurement surface for the producing of the image to compensate for the detected irregularities.

13. The device as claimed in claim 12, wherein the data processing device determines a local measurement density as an evaluation variable and weights the echo signals of the respective measurement positions that have relatively large local measurement densities with relatively small weightings.

14. The device as claimed in claim 13, wherein the data processing device determines the local measurement density from a representative number of detected measurement positions per unit area of the measurement surface, or per unit length of at least one scan line of the measurement surface.

15. The device as claimed in claim 13, wherein the data processing device determines the local measurement density by summing all of the reciprocals of all the distances of a detected measurement position in relation to all other detected measurement positions within a prescribed first radius.

16. The device as claimed in claim 13, further comprising weighting the echo signals of the respective measurement positions inverse proportion to the local measurement density.

17. The device as claimed in claim 13, further comprising weighting the echo signals of the respective measurement positions that have relatively large local measurement densities with zero.

18. The device as claimed in claim 17, wherein the data processing device redetermines the local measurement density within a prescribed second radius around the respective measurement positions having corresponding echo signals that have been weighted with zero.

19. The device as claimed in claim 17, wherein the data processing device removes the respective measurement positions weighted with zero, and redetermines the local measurement density as long as a prescribed minimum measurement density is at least equal to a predetermined measurement density.

20. The device as claimed in claim 13, further comprising determining a homogeneous contribution of all subareas of the measurement surface as the at least one evaluation variable and weighting the echo signals of the respective measurement positions to contribute as equally as possible to the image.

21. The device as claimed in claim 13, wherein the detecting device detects the respective measurement positions of the probe upon emission of the ultrasonic signal or upon reception of the corresponding echo signal.

22. The device as claimed in claim 13, wherein the probe is movable by hand along the surface of the test object.

* * * * *